(12) United States Patent
Hall et al.

(10) Patent No.: US 11,331,458 B2
(45) Date of Patent: May 17, 2022

(54) SUBCUTANEOUS VASCULAR ASSEMBLIES FOR IMPROVING BLOOD FLOW AND RELATED DEVICES AND METHODS

(71) Applicant: Merit Medical Systems, Inc., South Jordan, UT (US)

(72) Inventors: John Hall, North Salt Lake, UT (US); Lucia Irazabal, Holladay, UT (US); Westin Raines, Eagle Mountain, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 741 days.

(21) Appl. No.: 16/174,956

(22) Filed: Oct. 30, 2018

(65) Prior Publication Data

US 2019/0126017 A1    May 2, 2019

Related U.S. Application Data

(60) Provisional application No. 62/579,228, filed on Oct. 31, 2017.

(51) Int. Cl.
| | |
|---|---|
| *A61M 27/00* | (2006.01) |
| *A61L 29/04* | (2006.01) |
| *A61L 29/06* | (2006.01) |
| *A61L 29/14* | (2006.01) |

(Continued)

(52) U.S. Cl.
CPC ............. *A61M 27/002* (2013.01); *A61F 2/06* (2013.01); *A61L 29/02* (2013.01); *A61L 29/041* (2013.01); *A61L 29/06* (2013.01); *A61L 29/14* (2013.01); *A61F 2210/0076* (2013.01); *A61F 2230/0091* (2013.01); *A61M 2205/0216* (2013.01)

(58) Field of Classification Search
CPC ......... A61M 1/3655; A61M 2205/0216; A61F 2/06; A61F 2210/0076; A61F 2230/0091; A61L 29/02; A61L 29/041; A61L 29/06; A61L 29/14
See application file for complete search history.

(56) References Cited

U.S. PATENT DOCUMENTS

| | | |
|---|---|---|
| 3,357,432 A | 12/1967 | Sparks |
| 3,435,823 A | 4/1969 | Edwards |
| 3,490,438 A | 1/1970 | Lavender et al. |

(Continued)

FOREIGN PATENT DOCUMENTS

| | | |
|---|---|---|
| DE | 4418910 | 12/1995 |
| DE | 29515546 | 3/1997 |

(Continued)

OTHER PUBLICATIONS

Notice of Allowance dated Mar. 11, 2020 for U.S. Appl. No. 15/828,040.

(Continued)

*Primary Examiner* — Philip R Wiest
(74) *Attorney, Agent, or Firm* — Dorsey & Whitney LLP

(57) ABSTRACT

Reinforcing sleeves for medical device lumens are disclosed. In some embodiments reinforcing sleeves may provide resistance to crushing, kinking, or other deformation of the lumen. Reinforcing sleeves within the scope of this disclosure may be displaceable along an outer diameter of a reinforced lumen. Some reinforcing sleeves within the scope of this disclosure comprise metal alloys.

20 Claims, 7 Drawing Sheets

(51) Int. Cl.
  *A61L 29/02* (2006.01)
  *A61F 2/06* (2013.01)

(56) References Cited

U.S. PATENT DOCUMENTS

| | | | |
|---|---|---|---|
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmernan |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,550,447 A | 11/1985 | Seiler, Jr |
| 4,619,641 A | 10/1986 | Schanzer |
| 4,655,771 A | 4/1987 | Wallersten |
| 4,723,948 A | 2/1988 | Clark et al. |
| 4,734,094 A | 3/1988 | Jacob et al. |
| 4,743,251 A | 5/1988 | Barra |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,877,661 A | 10/1989 | House et al. |
| 4,898,591 A | 2/1990 | Jang et al. |
| 4,898,669 A | 2/1990 | Tesio |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,084,065 A * | 1/1992 | Weldon ............ A61F 2/06 600/37 |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,282,860 A | 2/1994 | Matsuno et al. |
| 5,330,500 A | 7/1994 | Song |
| 5,336,616 A | 8/1994 | Livesey et al. |
| 5,399,168 A | 3/1995 | Wadsworth |
| 5,405,320 A | 4/1995 | Twardowski et al. |
| 5,405,339 A | 4/1995 | Kohnen et al. |
| 5,454,790 A | 10/1995 | Dubrul |
| 5,474,268 A | 12/1995 | Yu |
| 5,474,563 A | 12/1995 | Myler et al. |
| 5,476,451 A | 12/1995 | Ensminger et al. |
| 5,496,294 A | 3/1996 | Hergenrother et al. |
| 5,509,897 A | 4/1996 | Twardowski et al. |
| 5,549,663 A | 8/1996 | Cottone, Jr. |
| 5,558,641 A | 9/1996 | Glantz et al. |
| 5,562,617 A | 10/1996 | Finch, Jr. et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,637,088 A | 6/1997 | Wenner et al. |
| 5,637,102 A | 6/1997 | Tolkoff et al. |
| 5,645,532 A | 7/1997 | Horgan |
| 5,647,855 A | 7/1997 | Trooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Schuster |
| 5,755,775 A | 5/1998 | Trerotola et al. |
| 5,792,104 A | 8/1998 | Speckman et al. |
| 5,797,879 A | 8/1998 | Decampli |
| 5,800,512 A | 9/1998 | Lentz et al. |
| 5,800,514 A | 9/1998 | Nunez et al. |
| 5,800,522 A | 9/1998 | Campbell |
| 5,810,870 A | 9/1998 | Myers et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,261,255 B1 | 7/2001 | Mullis et al. |
| 6,261,257 B1 | 7/2001 | Uflacker et al. |
| 6,280,466 B1 | 8/2001 | Kugler et al. |
| 6,308,992 B1 | 10/2001 | Mitsui et al. |
| 6,309,411 B1 | 10/2001 | Lashinski et al. |
| 6,319,279 B1 | 11/2001 | Shannon et al. |
| 6,338,724 B1 | 1/2002 | Dossa |
| 6,398,764 B1 | 6/2002 | Finch, Jr. et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,582,409 B1 | 6/2003 | Squitieri |
| 6,585,762 B1 | 7/2003 | Stanish |
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda et al. |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway et al. |
| 6,758,836 B2 | 7/2004 | Zawacki |
| 6,858,019 B2 | 2/2005 | McGuckin, Jr. et al. |
| 6,926,724 B1 | 8/2005 | Chu |
| 6,926,735 B2 | 8/2005 | Henderson |
| 6,976,952 B1 | 12/2005 | Maini et al. |
| 6,981,987 B2 | 1/2006 | Huxel et al. |
| 7,011,645 B2 | 3/2006 | McGuckin, Jr. et al. |
| 7,025,741 B2 | 4/2006 | Cull |
| 7,044,937 B1 | 5/2006 | Kirwan et al. |
| 7,101,356 B2 | 9/2006 | Miller |
| 7,131,959 B2 | 11/2006 | Blatter |
| 7,211,074 B2 | 5/2007 | Sansoucy |
| 7,244,271 B2 | 7/2007 | Lenz et al. |
| 7,244,272 B2 | 7/2007 | Dubson et al. |
| 7,252,649 B2 | 8/2007 | Sherry |

(56) References Cited

U.S. PATENT DOCUMENTS

| | | | |
|---|---|---|---|
| 7,297,158 B2 | 11/2007 | Jensen | |
| 7,351,257 B2 | 4/2008 | Kaldany | |
| 7,399,296 B2 | 7/2008 | Poole et al. | |
| 7,438,699 B2 | 10/2008 | Pecor et al. | |
| 7,452,374 B2 | 11/2008 | Hain et al. | |
| 7,507,229 B2 | 3/2009 | Hewitt et al. | |
| 7,588,551 B2 | 9/2009 | Gertner | |
| 7,708,722 B2 | 5/2010 | Glenn | |
| 7,722,665 B2 | 5/2010 | Anwar et al. | |
| RE41,448 E | 7/2010 | Squitieri | |
| 7,762,977 B2 * | 7/2010 | Porter | A61M 1/3655 |
| | | | 604/6.16 |
| 7,789,908 B2 | 9/2010 | Sowinski et al. | |
| 7,828,833 B2 | 11/2010 | Haverkost et al. | |
| 7,833,214 B2 | 11/2010 | Wilson et al. | |
| 7,846,139 B2 | 12/2010 | Zinn et al. | |
| 7,850,675 B2 | 12/2010 | Bell et al. | |
| 7,850,705 B2 | 12/2010 | Bach et al. | |
| 7,922,757 B2 * | 4/2011 | McGuckin, Jr. | A61F 2/064 |
| | | | 623/1.23 |
| 7,972,314 B2 | 7/2011 | Bizup et al. | |
| 8,079,973 B2 * | 12/2011 | Herrig | A61M 25/0014 |
| | | | 604/8 |
| 8,092,435 B2 | 1/2012 | Beling et al. | |
| 8,313,524 B2 | 11/2012 | Edwin et al. | |
| 8,388,634 B2 | 3/2013 | Rubenstein et al. | |
| 8,512,312 B2 | 8/2013 | Sage | |
| 8,551,139 B2 | 10/2013 | Surti et al. | |
| 8,690,815 B2 | 4/2014 | Porter et al. | |
| 8,951,355 B2 | 2/2015 | Clearflow et al. | |
| 9,642,623 B2 | 5/2017 | Agarwal et al. | |
| 2001/0053930 A1 | 12/2001 | Kugler et al. | |
| 2002/0049403 A1 | 4/2002 | Alanis | |
| 2002/0055766 A1 | 5/2002 | Wallace et al. | |
| 2002/0055771 A1 | 5/2002 | Sandock | |
| 2002/0099432 A1 | 7/2002 | Yee | |
| 2002/0151761 A1 | 10/2002 | Viole et al. | |
| 2003/0100859 A1 | 5/2003 | Henderson et al. | |
| 2003/0135258 A1 | 7/2003 | Andreas et al. | |
| 2003/0135261 A1 | 7/2003 | Kugler et al. | |
| 2003/0139806 A1 | 7/2003 | Haverkost et al. | |
| 2003/0181969 A1 | 9/2003 | Kugler et al. | |
| 2003/0212385 A1 | 11/2003 | Brenner et al. | |
| 2003/0212431 A1 | 11/2003 | Brady et al. | |
| 2004/0024442 A1 | 2/2004 | Sowinkski et al. | |
| 2004/0054405 A1 | 3/2004 | Thierry et al. | |
| 2004/0073282 A1 | 4/2004 | Stanish | |
| 2004/0078071 A1 | 4/2004 | Escamilla et al. | |
| 2004/0147866 A1 | 7/2004 | Blatter et al. | |
| 2004/0193242 A1 | 9/2004 | Lentz et al. | |
| 2004/0215058 A1 | 10/2004 | Zirps et al. | |
| 2004/0215337 A1 | 10/2004 | Hain et al. | |
| 2004/0236412 A1 | 11/2004 | Brar | |
| 2005/0004553 A1 | 1/2005 | Douk | |
| 2005/0137614 A1 | 6/2005 | Porter et al. | |
| 2005/0192559 A1 | 9/2005 | Michels et al. | |
| 2005/0203457 A1 | 9/2005 | Smego | |
| 2005/0209581 A1 | 9/2005 | Butts et al. | |
| 2005/0215938 A1 | 9/2005 | Khan et al. | |
| 2006/0004392 A1 | 1/2006 | Amarant | |
| 2006/0029465 A1 | 2/2006 | Auer | |
| 2006/0058867 A1 | 3/2006 | Thistle et al. | |
| 2006/0064159 A1 | 3/2006 | Porter et al. | |
| 2006/0081260 A1 | 4/2006 | Eells et al. | |
| 2006/0118236 A1 | 6/2006 | House et al. | |
| 2007/0038288 A1 | 2/2007 | Lye et al. | |
| 2007/0078412 A1 | 4/2007 | McGuckin, Jr. et al. | |
| 2007/0078416 A1 | 4/2007 | Eliasen | |
| 2007/0078438 A1 | 4/2007 | Okada | |
| 2007/0088336 A1 | 4/2007 | Dalton | |
| 2007/0123811 A1 | 5/2007 | Squitieri | |
| 2007/0135775 A1 | 6/2007 | Edoga et al. | |
| 2007/0140797 A1 | 6/2007 | Armstrong | |
| 2007/0142850 A1 | 6/2007 | Fowler | |
| 2007/0161958 A1 | 7/2007 | Glenn | |
| 2007/0167901 A1 | 7/2007 | Herrig et al. | |
| 2007/0168019 A1 | 7/2007 | Amplatz et al. | |
| 2007/0173868 A1 | 7/2007 | Bach et al. | |
| 2007/0191779 A1 | 8/2007 | Shubayev et al. | |
| 2007/0197856 A1 | 8/2007 | Gellman et al. | |
| 2007/0213838 A1 | 9/2007 | Hengelmolen | |
| 2007/0219510 A1 | 9/2007 | Zinn et al. | |
| 2007/0233018 A1 | 10/2007 | Bizup et al. | |
| 2007/0244539 A1 | 10/2007 | Lentz et al. | |
| 2007/0249986 A1 | 10/2007 | Smego | |
| 2007/0249987 A1 | 10/2007 | Gertner | |
| 2007/0265584 A1 | 11/2007 | Hickman et al. | |
| 2007/0293823 A1 | 12/2007 | Sherry | |
| 2007/0293829 A1 | 12/2007 | Conlon et al. | |
| 2008/0009781 A1 | 1/2008 | Anwar et al. | |
| 2008/0027534 A1 | 1/2008 | Edwin et al. | |
| 2008/0132924 A1 | 6/2008 | McGuckin | |
| 2008/0167595 A1 | 7/2008 | Porter et al. | |
| 2008/0221469 A1 | 9/2008 | Shevchuk | |
| 2008/0306580 A1 | 12/2008 | Jenson et al. | |
| 2009/0076587 A1 * | 3/2009 | Cully | A61F 2/82 |
| | | | 623/1.13 |
| 2009/0137944 A1 | 5/2009 | Haarala et al. | |
| 2009/0179422 A1 | 7/2009 | Werth | |
| 2009/0227932 A1 | 9/2009 | Herrig | |
| 2009/0234267 A1 | 9/2009 | Ross | |
| 2009/0318895 A1 | 12/2009 | Lachner | |
| 2010/0154800 A1 | 6/2010 | Chang et al. | |
| 2010/0160718 A1 | 6/2010 | Villafana et al. | |
| 2010/0198079 A1 | 8/2010 | Ross | |
| 2010/0268188 A1 | 10/2010 | Hanson | |
| 2010/0268196 A1 | 10/2010 | Hastings et al. | |
| 2010/0292774 A1 | 11/2010 | Shalev | |
| 2011/0015723 A1 | 1/2011 | Batiste et al. | |
| 2011/0054312 A1 | 3/2011 | Bell et al. | |
| 2011/0060264 A1 | 3/2011 | Porter et al. | |
| 2011/0112482 A1 | 5/2011 | Redd | |
| 2011/0208218 A1 | 8/2011 | Ball | |
| 2011/0257609 A1 | 10/2011 | Bizup et al. | |
| 2011/0264080 A1 | 10/2011 | Lim et al. | |
| 2011/0295181 A1 | 12/2011 | Dann et al. | |
| 2012/0059305 A1 | 3/2012 | Akingba | |
| 2012/0065652 A1 | 3/2012 | Cully et al. | |
| 2012/0078202 A1 | 3/2012 | Beling et al. | |
| 2013/0060268 A1 | 3/2013 | Herrig | |
| 2013/0338559 A1 | 12/2013 | Franano et al. | |
| 2014/0018721 A1 | 1/2014 | Gage et al. | |
| 2014/0094841 A1 | 4/2014 | Sutton et al. | |
| 2014/0276215 A1 | 9/2014 | Nelson | |
| 2014/0288638 A1 | 9/2014 | Knight et al. | |
| 2014/0371779 A1 | 12/2014 | Vale et al. | |
| 2015/0051532 A1 * | 2/2015 | Tomko | A61M 1/3661 |
| | | | 604/8 |
| 2015/0082604 A1 | 3/2015 | Cully et al. | |
| 2015/0094744 A1 * | 4/2015 | Aghayev | A61B 17/12045 |
| | | | 606/153 |
| 2015/0150640 A1 | 6/2015 | Boyle et al. | |
| 2016/0066954 A1 | 3/2016 | Miller et al. | |
| 2016/0129177 A1 | 5/2016 | Herrig | |
| 2016/0279317 A1 * | 9/2016 | Gale | A61M 1/3655 |
| 2017/0020556 A1 | 1/2017 | Sutton et al. | |
| 2019/0015627 A1 | 1/2019 | Hall et al. | |
| 2019/0022368 A1 | 1/2019 | Hall et al. | |
| 2019/0184151 A1 | 6/2019 | Herrig | |

FOREIGN PATENT DOCUMENTS

| | | |
|---|---|---|
| DE | 102008055587 | 8/2009 |
| EP | 1797831 | 6/2007 |
| JP | 62112567 | 5/1987 |
| JP | 04507050 | 12/1992 |
| JP | 05212107 | 8/1993 |
| JP | 06105798 | 4/1994 |
| JP | 09084871 | 3/1997 |
| JP | 09264468 | 7/1997 |
| JP | 2003501223 | 1/2003 |
| JP | 3995057 | 10/2007 |
| JP | 2008511414 | 4/2008 |
| KR | 101026933 | 4/2011 |

(56) References Cited

FOREIGN PATENT DOCUMENTS

| | | |
|---|---|---|
| KR | 1020110036848 | 4/2011 |
| WO | 198403036 | 8/1984 |
| WO | 199008509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001028456 | 4/2001 |
| WO | 2004032991 | 4/2004 |
| WO | 2004112880 | 12/2004 |
| WO | 2006026687 | 9/2006 |
| WO | 2009059371 | 5/2009 |
| WO | 2010059102 | 5/2010 |
| WO | 2011060386 | 5/2011 |
| WO | 2011153302 | 12/2011 |
| WO | 2012143922 | 10/2012 |
| WO | 2015100251 | 7/2015 |

OTHER PUBLICATIONS

Office Action dated Oct. 17, 2019 for U.S. Appl. No. 15/828,040.
Office Action dated Apr. 28, 2020 for U.S. Appl. No. 14/192,567.
Office Action dated May 1, 2020 for U.S. Appl. No. 15/693,010.
International Search Report and Written Opinion dated Apr. 4, 2019 for PCT/US2018/058179.
Office Action dated Aug. 21, 2019 for U.S. Appl. No. 14/192,567.
Office Action dated Sep. 26, 2019 for U.S. Appl. No. 15/693,010.
Lin, et al., Contemporary Vascular Access Surgery for Chronic Haemodialysis, They Royal College of Surgeons of Edinburgh, J.R. Coll, Surg, Edinb., 41 ,Jun. 1996 ,164-169.
Peterson, et al., Subclavian Venous Stenosis: A Complication of Subclavian Dialysis, The Journal of American Medical Association, vol. 252 No. 24 ,Dec. 28, 1994 ,3404-3406.
Raju M.D., et al., Techniques for Insertion and Management of Complications, PTFE Grafts for Hemodialysis Access, Ann. Surg., vol. 206 No. 5 ,Nov. 1987 ,666-673.
Sharafuddin, et al., Percutaneous Balloon-Assisted Aspiration Thrombectomy of clotted ahemodialysis Access Grafts, Journal of Vascular and Interventional Radiology, vol. 7 No. 2 ,Mar.-Apr. 1996, 177-183.
European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 18, 2019 for PCT/US2018/041821.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.

International Search Report and Written Opinion dated Jun. 3, 2009 for PCT/US2009/035923.
International Search Report and Written Opinion dated Jun. 15, 2018 for PCT/US2018/020614.
International Search Report and Written Opinion dated Jun. 20, 2007 for PCT/US2006/044564.
International Search Report and Written Opinion dated Jul. 17, 2018 for PCT/US2018/023956.
International Search Report and Written Opinion dated Oct. 30, 2018 for PCT/US2018/042900.
International Search Report and Written Opinion dated Jun. 22, 2018 for PCT/US2018/014371.
Notice of Allowance dated Mar. 15, 2010 for U.S. Appl. No. 11/216,536.
Notice of Allowance dated Oct. 4, 2013 for U.S. Appl. No. 12/831,092.
Notice of Allowance dated Oct. 5, 2018 for U.S. Appl. No. 15/093,622.
Notice of Allowance dated Nov. 6, 2018 for U.S. Appl. No. 14/995,270.
Office Action dated Jan. 8, 2019 for U.S. Appl. No. 15/035,626.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated Mar. 15, 2018 for U.S. Appl. No. 14/332,091.
Office Action dated May 5, 2010 for U.S. Appl. No. 10/962,200.
Office Action dated May 24, 2018 for U.S. Appl. No. 14/995,270.
Office Action dated Jun. 4, 2018 for U.S. Appl. No. 14/192,567.
Office Action dated Jun. 9, 2016 for U.S. Appl. No. 14/192,567.
Office Action dated Jun. 15, 2017 for U.S. Appl. No. 14/192,567.
Office Action dated Jul. 11, 2018 for U.S. Appl. No. 14/450,468.
Office Action dated Jul. 19, 2018 for U.S. Appl. No. 15/035,626.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 1, 2018 for U.S. Appl. No. 14/332,091.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 5, 2018 for U.S. Appl. No. 14/450,468.
Office Action dated Dec. 7, 2018 for U.S. Appl. No. 14/192,567.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Besarab, et al., Measuring the Adequacy of Hemodialysis Access, Current Opinion in Nephrology and Hypertension, Rapid Science Publishers ISSN ,1996 ,1062-4821.
Coulson MD, et al., Modification of Venous End of Dialysis Grafts: An Attempt to Reduce Neointimal Hyperplasia, Dialysis & Transplantation, vol. 29 No. Jan. 1, 2000 ,10-18.
Coulson MD, PHD, et al., A Combination of the Elephant Trunk Anastomosis Technique and Vascular Clips for Dialysis Grafts, Surgical Rounds ,Nov. 1999 ,596-608.
Kanterman, et al., Dialysis Access Grafts: Anatomic Location of Venous Stenosis and Results of Angioplasty, Interventional Radiology, vol. 195 No. 1, 195 ,Apr. 1995 ,135-139.
Kumpe, et al., Angioplasty/Thrombolytic Treatment of Failing and Failed Hemodialysis Access Sites: Comparison with Surgical Treatment, Progress in Cardiovascular Diseases, vol. XXXIV No. 4 ,Jan./Feb. 1992 ,263-278.
Office Action dated Apr. 6, 2021 for U.S. Appl. No. 16/284,526.
European Search Report dated Jul. 8, 2021 for EP18874078.1.

* cited by examiner

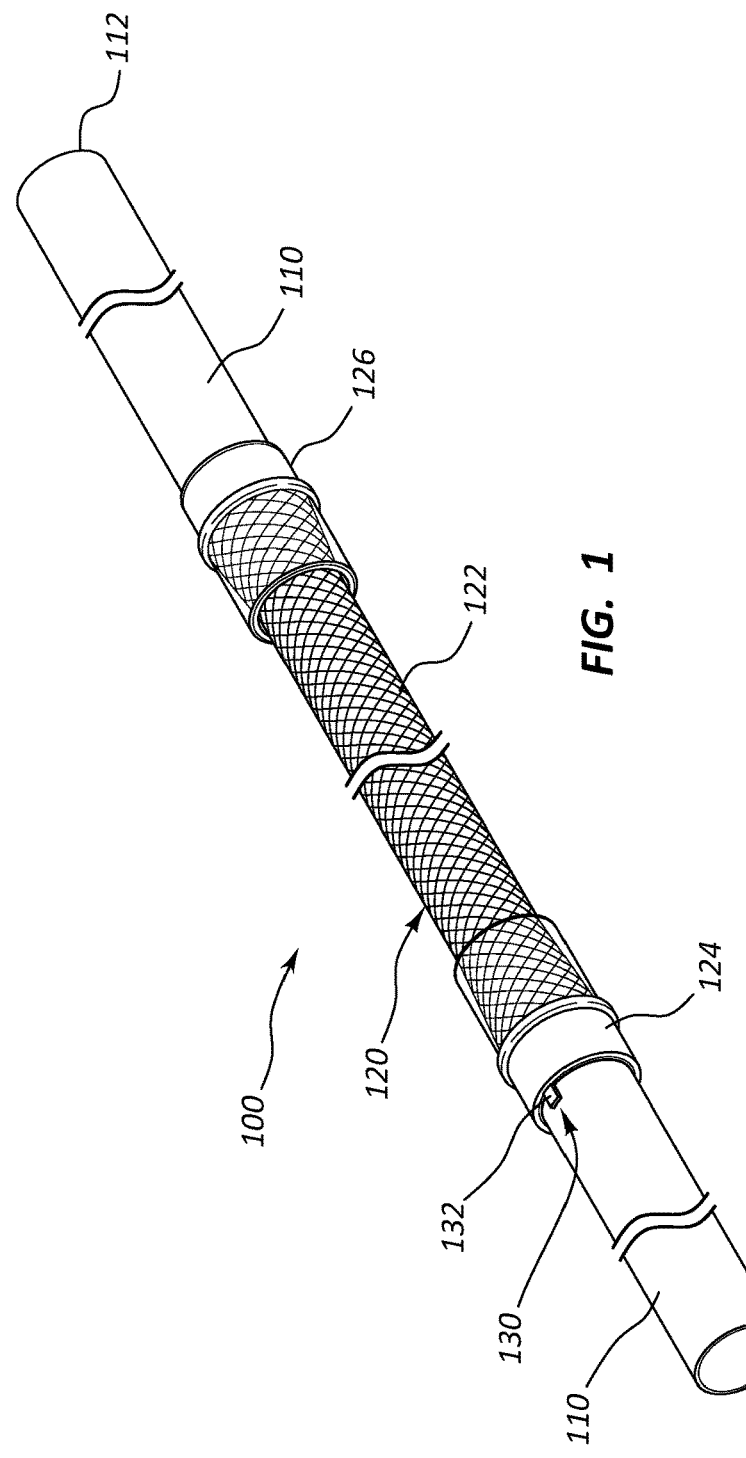
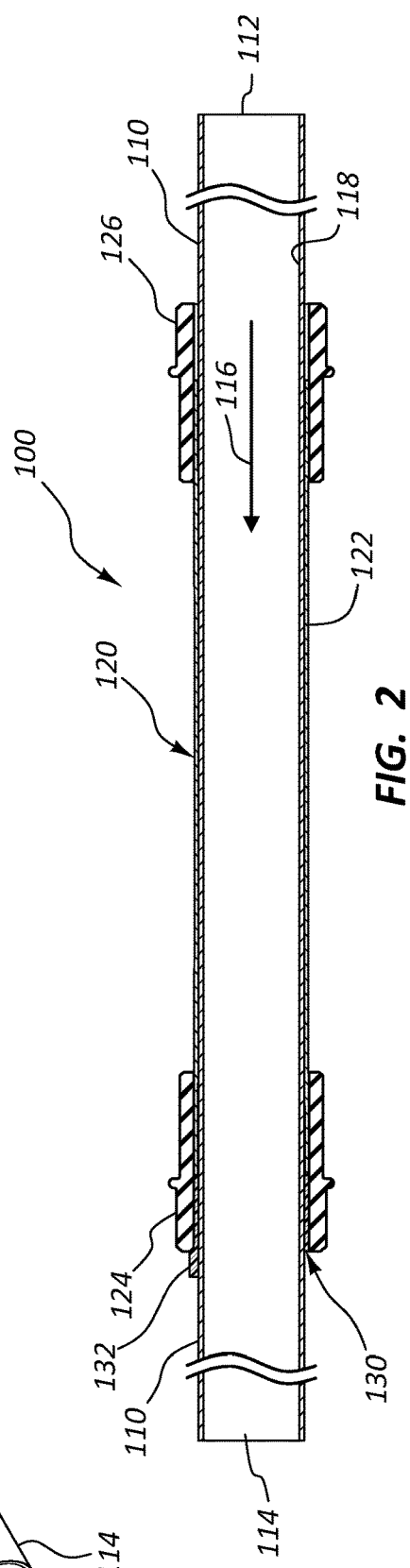

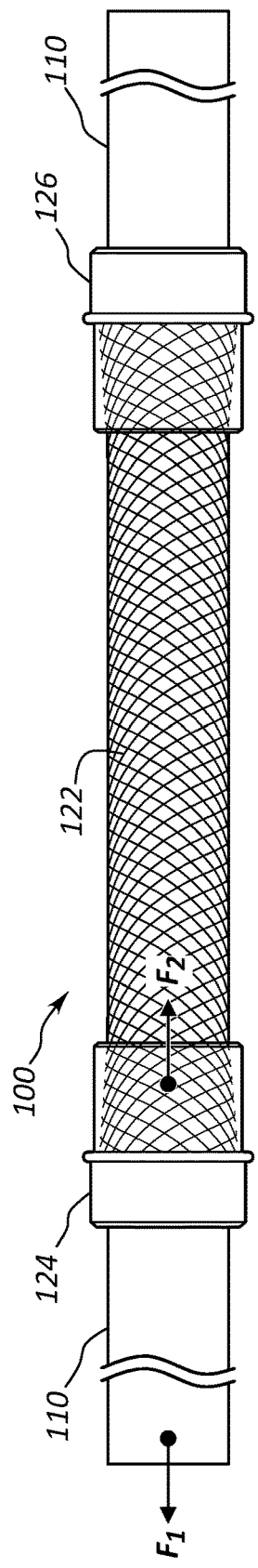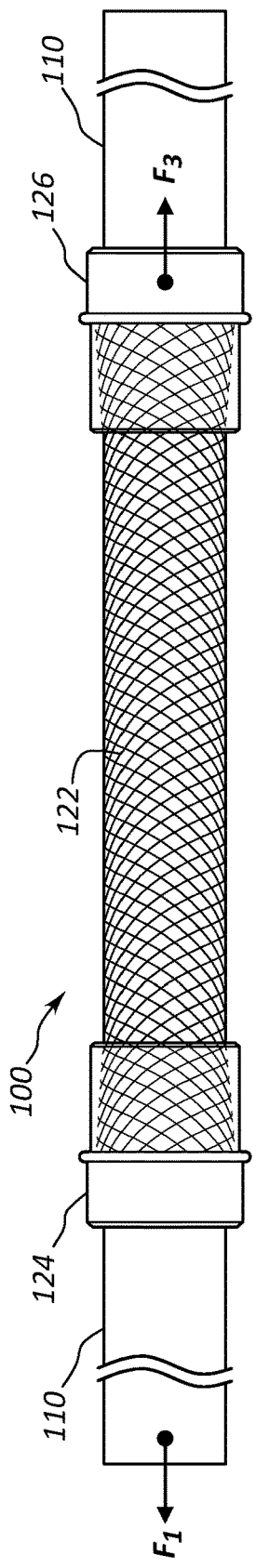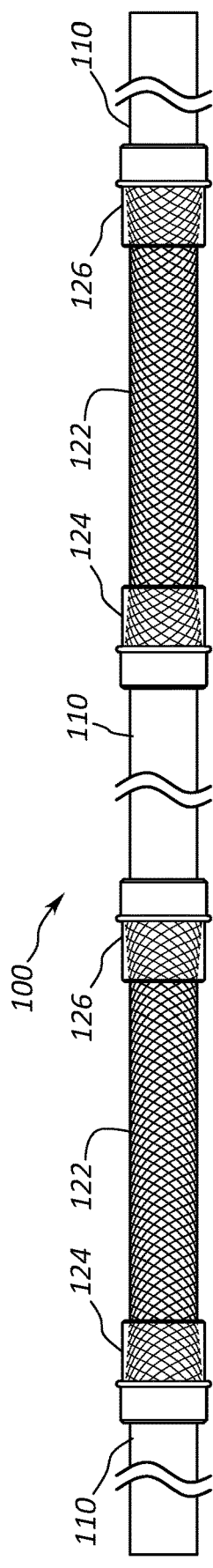

SUBCUTANEOUS VASCULAR ASSEMBLIES FOR IMPROVING BLOOD FLOW AND RELATED DEVICES AND METHODS

RELATED APPLICATIONS

This application claims priority to U.S. Provisional Application No. 62/579,228, filed on Oct. 31, 2017 and titled, "SUBCUTANEOUS VASCULAR ASSEMBLIES FOR IMPROVING BLOOD FLOW AND RELATED DEVICES AND METHODS," which is hereby incorporated by reference in its entirety.

TECHNICAL FIELD

The present disclosure relates generally to the field of medical devices. More particularly, some embodiments relate to medical assemblies and devices for improving blood flow to regions of a patient's body.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 is a perspective view of a medical device, according to an embodiment.

FIG. 2 is cross-sectional side view of the medical device of FIG. 1.

FIG. 5 is a side view of the medical device of FIG. 1 with a push force being applied to the reinforcing sleeve.

FIG. 6 is a side view of the medical device of FIG. 1 with a pull force being applied to the reinforcing sleeve.

FIG. 7 is a side view of the medical device of FIG. 1 with a plurality of reinforcing sleeves.

DETAILED DESCRIPTION

Figure 3:
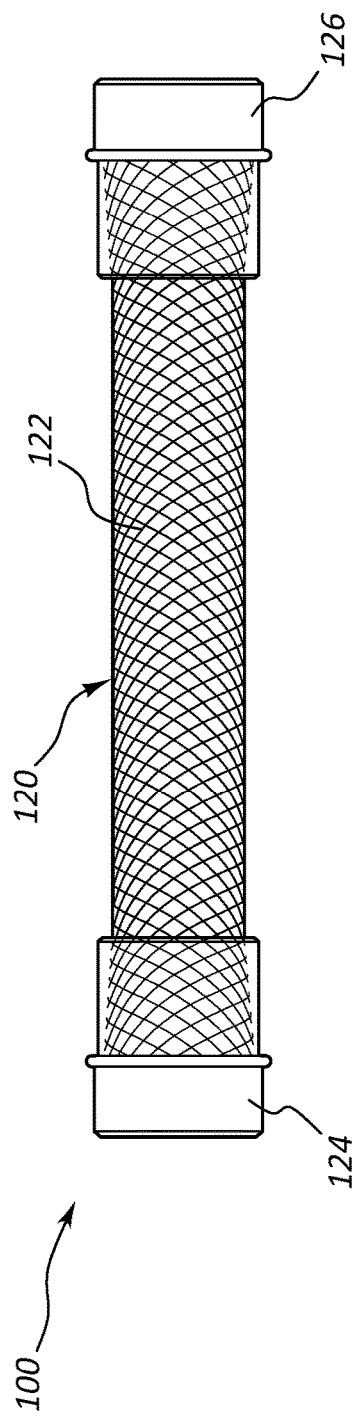
FIG. 3 is a perspective view of a reinforcing sleeve of the medical device of FIG. 1, according to an embodiment.

Many individuals suffer from insufficient blood flow to regions (e.g., peripheral regions) of their body. For example, some individuals suffering from peripheral artery disease experience narrowing of one or more peripheral arteries (e.g., a superficial femoral artery) to their leg(s) or arm(s). Such narrowing of the arteries may reduce blood flow to one or more peripheral regions. Insufficient blood flow to the extremities of the body can lead to critical limb ischemia, gangrene, and/or amputation. Diabetes is known to increase the risk of peripheral artery disease.

Insufficient blood flow to peripheral regions of a body may result from other causes as well. For example, in addition to atherosclerosis in peripheral arteries, blood flow to a peripheral region may be impeded by some other blockage. In other cases, a portion of an artery may be punctured or weakened, thereby rendering the artery (or a portion of the artery) unsuitable for providing long-term blood flow to a peripheral region.

Embodiments described herein may be used to form a non-natural flow path that improves blood flow to regions of a patient. For example, in some embodiments, a medical device that includes a first graft portion, a second graft portion, and a catheter portion that is coupled to and disposed between the first graft portion and the second graft portion may be inserted into a patient such that the first graft portion is coupled to the vasculature at a first location that is above the knee of a patient, and the second graft portion is coupled to the vasculature at a second location that is below the knee of the patient. The new flow path that is established between the first location and the second location may improve blood flow to a region (e.g., the lower leg or foot) of the patient.

The components described herein may additionally or alternatively be used to establish other non-natural flow paths within a patient. In some embodiments, both ends of the non-natural flow path are coupled to vasculature of the patient. In other embodiments, only one end of the non-natural flow path is coupled to vasculature of the patient. In some embodiments, the non-natural flow path is disposed within the torso region of the patient. In other embodiments, the non-natural flow path is disposed below the waist. In some embodiments, the non-natural flow path extends from above the waist to below the waist. In some embodiments, the non-natural flow path traverses the knee (i.e., connects the upper leg with the lower leg). In some embodiments, one end of the non-natural flow path empties directly into a chamber of the heart. Other suitable locations for non-natural flow paths formed by medical devices described herein are possible and within the scope of this disclosure.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to one another through an intermediate component. The phrase "attached to" refers to interaction between two or more entities which are in direct contact with each other and/or are separated from each other only by a fastener of any suitable variety (e.g., an adhesive).

As used herein, the term "crush force" refers to the magnitude of a two-dimensional force (e.g., pinch force) that is applied perpendicular to the longitudinal axis of a tube that causes deformation of the tube from an unconstrained state to a constrained state in which the distance between opposite sides of the tube is three-quarters of the distance between opposite sides of the tube when the tube is unconstrained. As used herein, the term "hoop force" refers to the magnitude of a force that is uniformly applied around a circumference of a tube to compress the tube to three-quarters of its initial diameter. A "porous tube" is considered to be porous even if the porous tubular structure is coated, disposed between, or embedded within a non-porous polymer. For example, a tubular wire structure that includes openings between adjacent elements of wire is porous even if the tubular wire structure is coated, disposed between, or embedded within a non-porous polymer.

Figure 4:
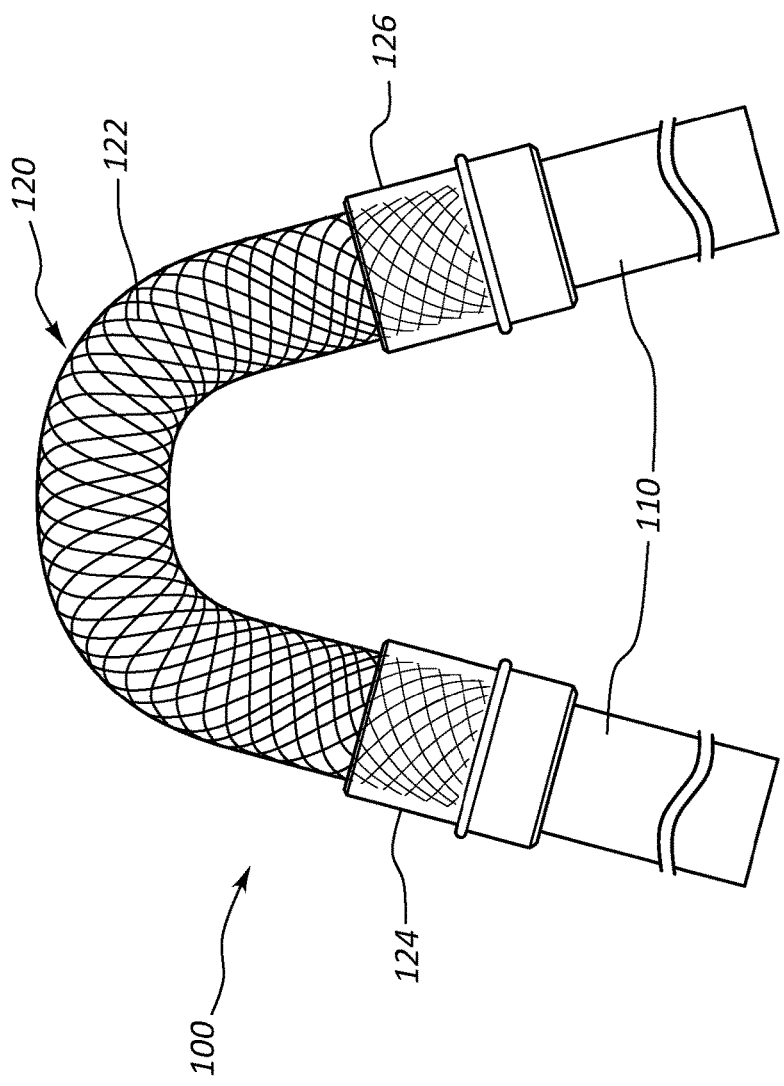
FIG. 4 is a side view of the medical device of FIG. 1 in a bent configuration.

FIGS. 1-7 provide alternative views of a medical device 100 (or a portion thereof) that establishes a non-natural flow path for improving blood flow to a region of a patient, such as a lower leg, a foot, an arm, or a hand. More specifically, FIG. 1 provides a perspective view of medical device 100. FIG. 2 provides a cross-sectional view of medical device 100. FIG. 3 provides a perspective view of a reinforcing sleeve 120. FIG. 4 provides a perspective view of medical device 100 with reinforcing sleeve 120 in a bent configuration. FIG. 5 provides a side view of medical device 100 with a push force being applied to reinforcing sleeve 120. FIG. 6 illustrates a side view of medical device 100 with a pull force being applied to reinforcing sleeve 120. FIG. 7 illustrates medical device 100 with multiple reinforcing sleeves 120.

As shown in FIGS. 1-7, medical device 100 includes a lumen 110 that has a tubular structure and a reinforcing sleeve 120. A first end 112 of lumen 110 is configured to couple by anastomosis to a first portion of a vasculature of a patient, such as a vein or artery, and a second end 114 of lumen 110 is configured to couple by anastomosis to a second portion of the vasculature of the patient. Lumen 110 provides a flow path 116 from the first portion of the vasculature to the second portion of the vasculature to bypass a narrowed, obstructed, damaged, and/or diseased portion of the vasculature. Lumen 110 may have an inner lining 118 that provides a continuous and smooth luminal surface for blood flow. Such a luminal surface may reduce blood turbulence and clotting in lumen 110. In some embodiments, inner lining 118 is made of a porous material. In some embodiments, inner lining 118 of lumen 110 is configured to permit tissue ingrowth. In some embodiments, inner lining 118 of lumen 110 is configured to provide an antithrombotic surface and/or an anti-inflammatory surface.

Lumen 110 may be synthetic, biologic, or a native vessel. In some embodiments, lumen 110 may be formed from a relatively flexible material. In addition, lumen 110 may be formed from a material that is suitable for anastomosis to a vein or artery of a patient. Suitable materials include, but are not limited to Polytetrafluoroethylene (PTFE), silicone, polyurethane, fluoroelastomers, fluorosilicone, PEBAX, and the like.

In some embodiments, lumen 110 may comprise multiple layers. For example, lumen 110 may have an inner layer formed from a polymer, such as porous PTFE. More specifically, the inner layer may be formed from expanded PTFE or fibrous PTFE. In embodiments that use fibrous PTFE, the fibrous PTFE may be formed by rotation of a spinneret (i.e., rotational spun PTFE) and/or by subjecting a solution or dispersion comprising PTFE to an electric field (i.e., electrospun PTFE).

Lumen 110 may also include an outer (i.e., abluminal) layer. Like the inner layer, the outer layer may be formed from a polymer such as porous PTFE. In some embodiments, the outer layer is configured to permit tissue ingrowth. In some embodiments, the outer layer is identical in composition to the inner layer. In other embodiments, the outer layer and the inner layer differ in composition.

In some embodiments, lumen 110 may include an intervening layer that is disposed between the inner layer and the outer layer. For example, in some embodiments, the intervening layer comprises one or more of silicone, fluorinated ethylene propylene (FEP), and polyether block amide (e.g., PEBAX). In some embodiments, the intervening layer may be an elastomeric material, such as silicone, that allows for resealing of lumen 110 after puncture. In other words, in some embodiments, at least a portion of lumen 110 may be pierced by a needle or other sharp object. Once the needle or other sharp object is retracted from lumen 110, the intervening layer may reseal about the aperture formed by the inserted needle or sharp object, thereby preventing the leakage of blood or other fluid across a wall of lumen 110. Such resealability may permit early cannulation of lumen 110 (e.g., cannulation within one week of implantation). In some embodiments, the silicone layer may be extruded silicone, and form an extruded silicone tube. Extruded silicone may have residual stresses that increase the resealability of the intervening layer. In some embodiments, the silicone layer may be the outer layer of lumen 110. In some embodiments, the silicone layer may be the inner layer of the lumen 110. The elastomeric material may provide increased durability after cannulation resulting in increased life and a smaller biological response. The self-sealing nature of the layer may provide several benefits, such as, reduced thrombus production, increased mechanical integrity of lumen 110, and reduced flow disturbances within lumen 110.

The length of lumen 110 is dependent on the situation in which lumen 110 is used to create a non-natural flow path. As discussed previously, lumen 110 enables a bypass of a narrowed, obstructed, damaged, and/or diseased portion of the patient's vasculature. The length of lumen 110 may be determined by (1) the desired location for placement in the patient and/or (2) the particular anatomy of the patient. The length of lumen 110 may be customizable, and a medical professional may trim the length of lumen 110 to meet the specific situation of a particular patient.

FIG. 3 illustrates reinforcing sleeve 120. Reinforcing sleeve 120 is configured to slide along lumen 110 to enable a medical professional to position reinforcing sleeve 120 to a desired location to reinforce and strengthen lumen 110. Reinforcing sleeve 120 may strengthen various types of lumens 110, such as synthetic, biologic, and native vessels, as previously discussed. The length of lumen 110 may vary depending on the situation of the patient. Since lumen 110 may be made from a relative flexible material, lumen 110 may be susceptible to damage or tearing. Reinforcing sleeve 120 is designed to increase the hoop strength, crush resistance, and longitudinal strength of lumen 110. In some embodiments, reinforcing sleeve 120 has a crush force that is greater than lumen 110. The high crush force of reinforcing sleeve 120 may prevent or reduce the risk of collapse of lumen 110. In some embodiments, reinforcing sleeve 120 has a hoop force that is greater than lumen 110. Due to the relatively high crush force and/or hoop force of reinforcing sleeve 120, reinforcing sleeve 120 may be suited for positioning within a patient where strength and/or crush resistance is warranted. For example, reinforcing sleeve 120 may be designed to be positioned adjacent to bones or ligaments that might cause the collapse of lumen 110, which is formed from weaker materials. In some embodiments, reinforcing sleeve 120 is positioned adjacent relatively sharp anatomy or in locations in which there is significant movement, such as joints like knees, ankles, hips, wrists, elbows, etc. In some embodiments, reinforcing sleeve 120 is designed to traverse a relatively sharp bend without kinking. The reinforcing sleeve 120 may additionally or alternatively be designed to be positioned at a relatively exposed location that is likely to be subjected to compression forces with some frequency. In other words, reinforcing sleeve 120 may be positioned along lumen 110 within the patient at a location where strength is warranted and/or along the portion of the flow path that is most likely to fail or necessitate replacement.

Reinforcing sleeve 120 includes a reinforcing structure 122 that is designed to increase the hoop strength, crush resistance, and longitudinal strength of lumen 110. Reinforcing structure 122 may be formed by braiding, as illustrated in FIG. 3. The braided structure may provide a crush force greater than the crush force of lumen 110.

Reinforcing structure 122 may comprise and/or consist of a metal alloy that is inert in the human body. For example, in some embodiments, reinforcing structure 122 comprises and/or consists of a nickel-titanium alloy, such as nitinol.

Reinforcing sleeve 120 may further include end caps 124 and 126 to prevent fraying of reinforcing structure 122. End caps 124 and 126 may also provide a location for the medical professional to grip reinforcing sleeve 120 and to slide reinforcing sleeve 120 along lumen 110. End caps 124 and 126 may comprise an inert material in a human body, such as silicone, PTFE, etc.

FIG. 4 illustrates medical device 100 and reinforcing sleeve 120 in a bent configuration. In some situations, medical device 100 is bent in order to create a flow path from a first portion of the vasculature to a second portion of the vasculature. In these situations, there is the possibility that lumen 110 may become kinked and substantially limit or decrease the flow through lumen 110. In these situations, reinforcing sleeve 120 may be positioned at the bending location to reinforce the bend and also prevent kinking of lumen 110. Reinforcing sleeve 120 may bend up to at least 180 degrees, as illustrated in FIG. 4, and prevent kinking of lumen 110. This may be beneficial if lumen 110 needs to make a sharp turn in order to create a non-natural flow path.

As discussed previously, reinforcing sleeve 120 may be placed on lumen 110 and the position of reinforcing sleeve 120 may be adjusted by sliding reinforcing sleeve 120 relative to lumen 110. To slide reinforcing sleeve 120 along lumen 110, a push force may be applied to reinforcing sleeve 120. FIG. 5 illustrates a force F1 being applied to lumen 110 in a first direction and a force F2 applied to end cap 124 closest to force F1 in a second direction, resulting in a net push force on the reinforcing sleeve 120. Accordingly, when the push force is applied to reinforcing sleeve 120, the medical professional may slide reinforcing sleeve 120 relative to lumen 110 to a predetermined location. The predetermined location may be determined by the medical professional to reinforce lumen 110 at specific locations where lumen 110 may be susceptible to damage or tearing.

Alternatively, if a pull force is applied to reinforcing sleeve 120, reinforcing sleeve 120 locks up and secures to lumen 110. For example, if a force F3 is applied to end cap 126 in the second direction farthest from force F1 applied in the first direction, as illustrated in FIG. 6 and resulting in a net pull force on the reinforcing sleeve 120, the reinforcing sleeve 120 locks to lumen 110. The structure of reinforcing sleeve 120 may determine how reinforcing sleeve 120 locks or secures to lumen 110. The structure of braided reinforcing structure 122 of reinforcing sleeve 120 clamps to lumen 110 when a pull force is applied to reinforcing sleeve 120. The braids of reinforcing structure 122 tighten and clamp against lumen 110 to lock reinforcing sleeve 120 in place.

Reinforcing sleeve 120 may be secured to lumen 110 by a number of different methods. After reinforcing sleeve 120 is positioned by the medical professional along lumen 110 to the predetermined position, the medical professional may secure or lock reinforcing sleeve 120 to lumen 110. For example, reinforcing sleeve 120 may be secured to lumen 110 by adhesives, fasteners, and the like. Alternately, reinforcing sleeve 120 may be simply be placed in the predetermined position and secured in place by the braids of reinforcing sleeve 120. In some embodiments, reinforcing structure 122 is configured to allow tissue ingrowth to secure reinforcing sleeve 120 in place. In some embodiments, reinforcing sleeve 120 is not secured to lumen 110, but is simply secured by tissue ingrowth.

In some embodiments, the diameter of end caps 124 and 126 is slightly smaller than the outer diameter of lumen 110. Because the inner diameter of end caps 124 and 126 is slightly smaller than the outer diameter of lumen 110, reinforcing sleeve 120 is secured in the predetermined location. Further, because the inner diameter of end caps 124 and 126 is only slightly smaller than the outer diameter of lumen 110, flow through lumen 110 is only slightly affected or not impacted at all. In some embodiments, end caps 124 and 126 may include an enlarging ring 130. FIGS. 1 and 2 illustrate enlarging ring 130 placed inside the inner diameter of end cap 124, which enlarges the diameter of end cap 124 because enlarging ring 130 has a diameter slightly larger than the outer diameter of lumen 110 and larger than the natural diameter of end cap 124. Accordingly, the medical professional may slide reinforcing sleeve 120 to the predetermined location, and once reinforcing sleeve 120 is in the predetermined location, the medical professional may remove enlarging ring 130 by pulling on enlarging ring tab 132. Once enlarging ring 130 is removed, end cap 124 may restrict to its natural diameter, which is slightly smaller than the outer diameter of lumen 110, allowing end cap 124 to slightly grip lumen 110.

In some embodiments, medical device 100 may include multiple reinforcing sleeves 120 along lumen 110, as illustrated in FIG. 7. For example, if the flow path includes multiple locations that may be susceptible to crushing or tearing and where strength and/or crush resistance is warranted, multiple reinforcing sleeves 120 may be used in various locations along lumen 110 to reinforce lumen 110.

Figure 8:
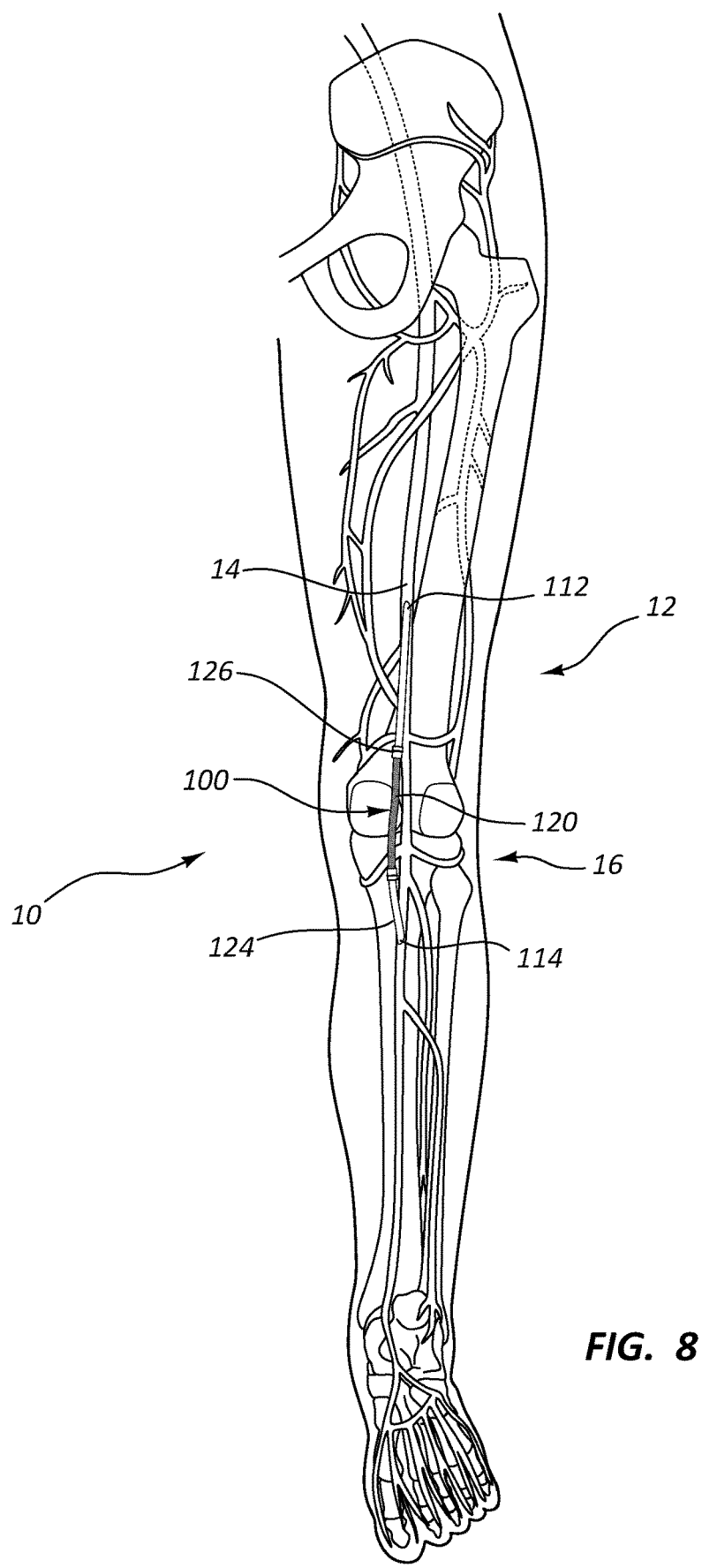
FIG. 8 is a posterior view of a leg of a patient into whom the medical device of FIG. 1 has been implanted.

FIG. 8 illustrates medical device 100 implanted into a leg 12 of a patient 10. First end 112 of lumen 110 is coupled to the femoral artery 14 above the knee 16 of patient 10, while second end 114 of lumen 110 is coupled to femoral artery 14 below the knee 16 of patient 10, thereby bypassing a damaged portion of femoral artery 14. Reinforcing sleeve 120 is positioned along lumen 110 above the knee 16 of patient 10. Since the knee 16 undergoes a lot of movement, lumen 110 may be susceptible to damage. Accordingly, the medical professional may reinforce lumen 110 by adjusting the position of reinforcing sleeve 120. Additionally, more reinforcing sleeves 120 may be placed along lumen 110 to ensure that the flow path is protected. In other embodiments, medical device 100 is implanted at another location within patient 10, such as a foot, arm, or hand.

Figure 9:
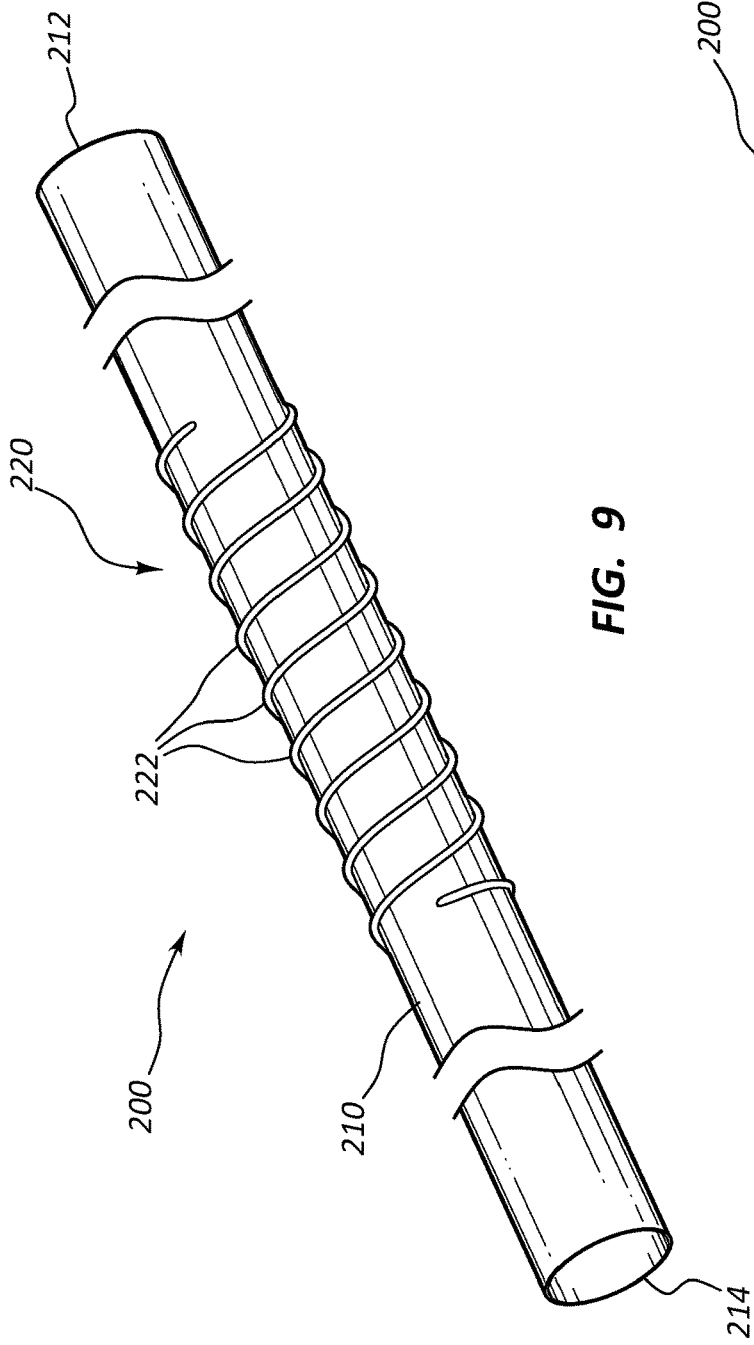
FIG. 9 is a perspective view of a medical device, according to an embodiment.
Figure 10:
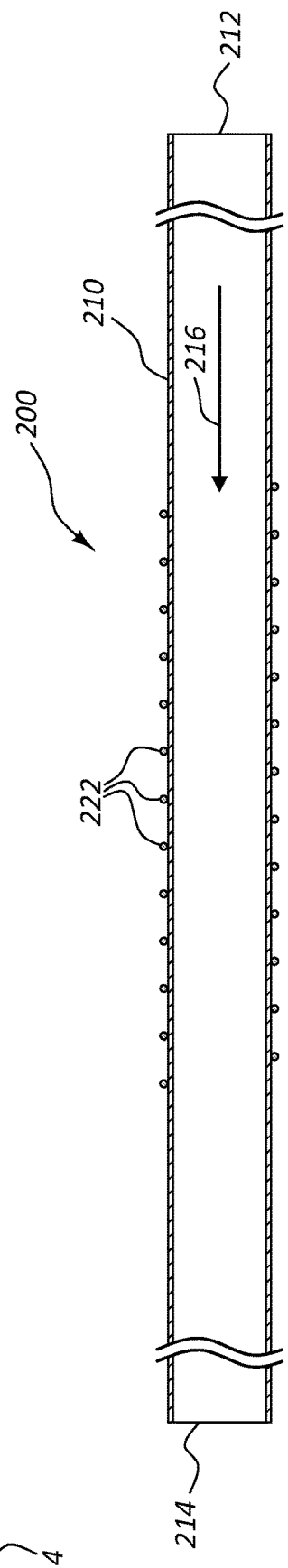
FIG. 10 is a cross-sectional side view of the medical device of FIG. 9.
Figure 11:
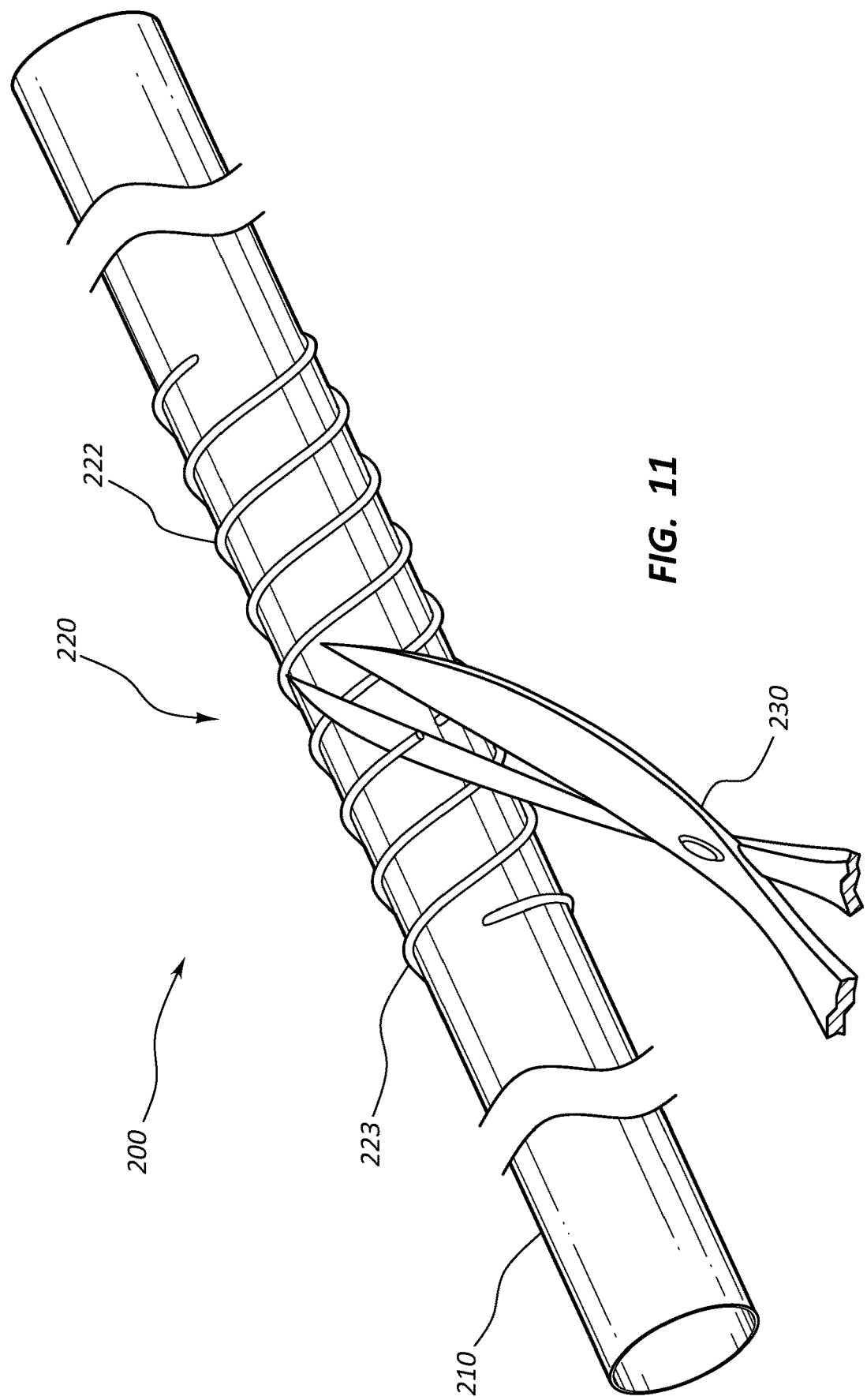
FIG. 11 is a perspective view of adjusting the length of a reinforcing sleeve of the medical device of FIG. 9.

FIGS. 9-11 depict an embodiment of a medical device 200 that resembles medical device 100 described above in certain respects. Accordingly, like features are designated with like reference numerals, with the leading digits incremented to "2." For example, the embodiment depicted in FIGS. 9-11 include a lumen 210 that may, in some respects, resemble the lumen 110 of FIGS. 1-7. Relevant disclosure set forth above regarding similarly identified features thus may not be repeated hereafter. Moreover, specific features of medical device 100 and related components shown in FIGS. 9-11 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical device 200 and related components depicted in FIGS. 9-11. Any suitable combination of the features, and variations of the same, described with respect to the medical device 100 and related components illustrated in FIGS. 1-7 can be employed with the medical device 200 and related components of FIGS. 9-11, and vice versa. This pattern of disclosure applies equally to further embodiments depicted in subsequent figures and described hereafter, wherein the leading digits may be further incremented.

FIGS. 9-11 provide alternative views of medical device 200 (or a portion thereof) for improving blood flow to a region of a patient, such as a lower leg, a foot, an arm, or a hand. FIG. 9 illustrates medical device 200 with a lumen 210 and a reinforcing sleeve 220. Reinforcing sleeve 220 may include a reinforcing structure 222 that may be formed by winding (e.g., helically winding or coiling) a metal alloy. Reinforcing structure 222 may comprise and/or consist of a metal alloy that is inert in the human body. For example, in some embodiments, reinforcing structure 222 comprises and/or consists of a nickel-titanium alloy, such as nitinol. FIG. 10 illustrates a cross-sectional side view of medical device 200. Reinforcing structure 222 winds around lumen 210 to increase the crush resistance of lumen 210.

In some embodiments, similar to reinforcing sleeve 120, reinforcing sleeve 220 is configured to slide over lumen 210 and may be positioned to a predetermined location. In some embodiments, reinforcing sleeve 220 may be secured to lumen 210 by clamping, suturing, adhesive, and the like. In some embodiments, reinforcing sleeve 220 may be stretched and tightened on lumen 210 to secure reinforcing sleeve 220. In some embodiments, reinforcing sleeve 220 may be configured to allow tissue ingrowth to help secure reinforcing sleeve 220 in place. In some embodiments, reinforcing sleeve 220 is not secured to lumen 210 but is simply secured by tissue ingrowth. In other embodiments, end caps 224 and 226 (shown on FIG. 12) may have a slightly smaller diameter than the outer diameter of lumen 110.

The length of reinforcing sleeve 220 may be adjusted in a number of different ways. In some embodiments the length of reinforcing sleeve 220 may be adjusted by stretching reinforcing sleeve 220 to make reinforcing sleeve 220 longer. In some embodiments, reinforcing sleeve may be cut or trimmed by a cutting element 230 (scissors, scalpel, etc.), as illustrated in FIG. 11. The medical professional may remove a trimmed portion 223 to shorten the length of reinforcing structure 222 and reinforcing sleeve 220.

Figure 12:
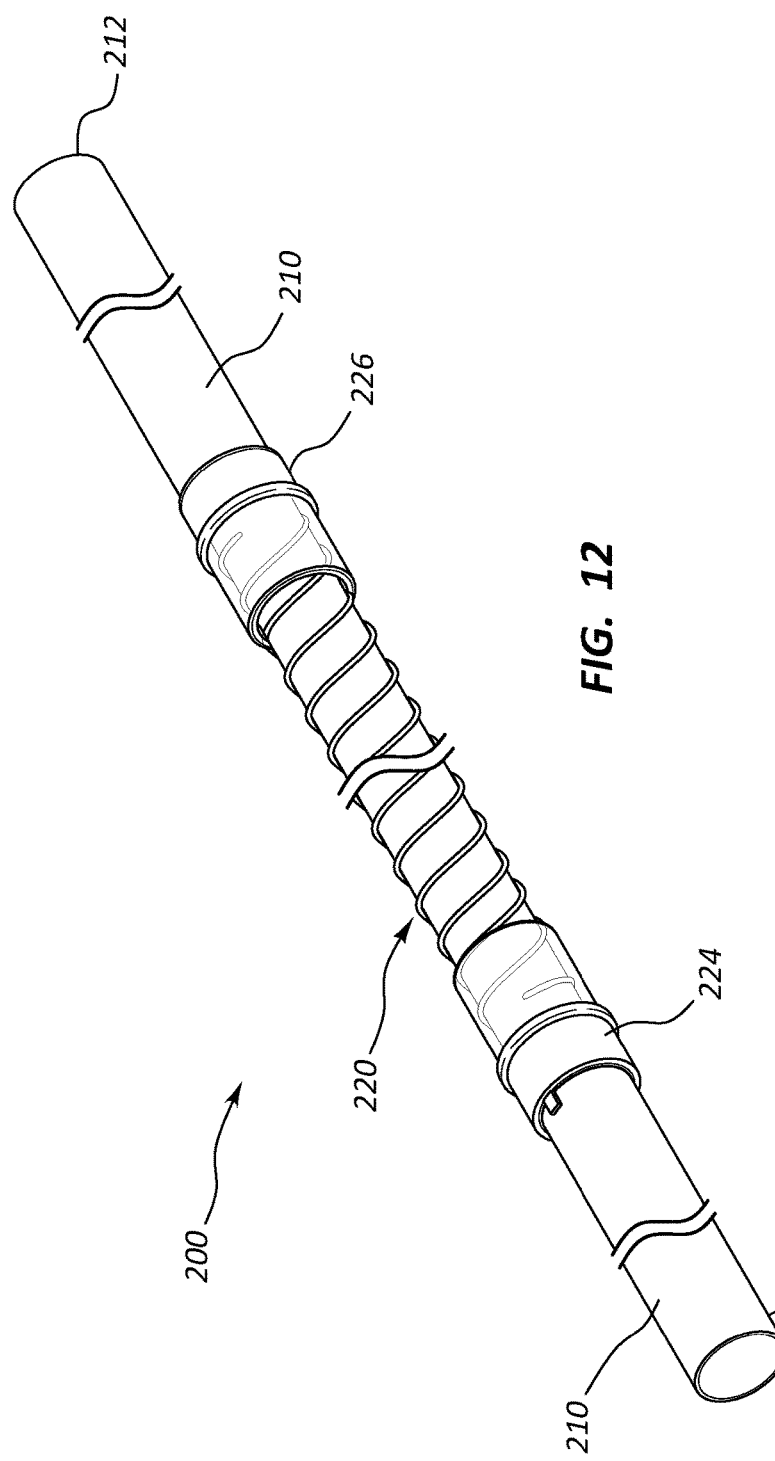
FIG. 12 is a perspective of the medical device of FIG. 9 with attachable end caps according to an embodiment.

In some embodiments, as illustrated in FIG. 12, reinforcing sleeve 220 may further include end caps 224 and 226. End caps 224 and 226 may also provide a location for the medical professional to grip reinforcing sleeve 220 and to slide reinforcing sleeve 220 along lumen 210. As discussed previously, the medical professional may stretch reinforcing sleeve 220 by gripping end caps 224 and 226.

In some embodiments, end caps 224 and 226 may be attachable and detachable from reinforcing structure 222. For example, the medical professional may cut reinforcing structure 222 and remove end cap 224 attached to the trim portion 223 and replace end cap 224 on the uncapped end of reinforcing structure 222. End caps 224 and 226 may comprise an inert material in a human body, such as silicone, PTFE, etc.

In some embodiments, reinforcing sleeve 220 may be bent similar to reinforcing sleeve 120 illustrated in FIG. 4. Reinforcing sleeve 220 may bend up to at least 180 degrees and may prevent kinking of lumen 210. In addition, coiled reinforcing structure 222 may be as flexible as lumen 110.

Figure 13:
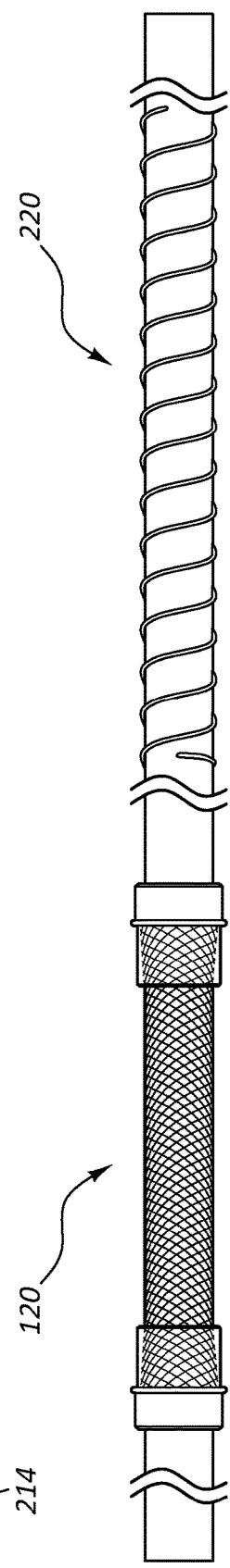
FIG. 13 is a side view of an embodiment of a medical device with a plurality of reinforcing sleeves.

In some embodiments, medical device 200 may include multiple reinforcing sleeves 220 along lumen 210. In some embodiments, medical device 200 may include different types of reinforcing sleeves, such as a reinforcing sleeve 120 with a braided reinforcing structure and a reinforcing sleeve 220 with a coiled reinforcing structure, as illustrated in FIG. 13. As each reinforcing sleeve 120 and 220 provides different benefits, the medical professional may decide to use reinforcing sleeve 120 in certain situations and reinforcing sleeve 220 in other situations.

In some embodiments, lumens 110 and 210 may be cannulated through reinforcing sleeves 120 and 220 as braided reinforcing structure 122 and coiled reinforcing structure 222 moves out of the way to enable the needle to pass through lumen 110.

In some embodiments, coiled reinforcing structure 222 may have a higher hoop force than braided reinforcing structure 122. In some embodiments, coiled reinforcing structure 222 may have a higher crush force than braided reinforcing structure 122.

The above disclosure has disclosed braided reinforcing structures 122 and wound reinforcing structures 222. However, the present disclosure is not so limited. Reinforcing sleeves may have a number of different structures to reinforce lumen 110, and it would be apparent to those having skill in the art that changes may be made to the structure of the reinforcing sleeves without departing from the underlying principles of the present disclosure.

Some embodiments relate to a kit for establishing a non-natural flow path within a patient. The kit may include, inter alia, the following components: a lumen 110, a plurality of reinforcing sleeves (e.g., 120, 220, etc.) with a variety of different reinforcing structures (122, 222, etc.) of varying length, cutting element 230, and instructions for creating a non-natural flow path within the patient. Cutting element 230 may be used to adjust the length of lumen 110, 210 or adjust the length of reinforcing sleeves 120 and 220.

In some embodiments, medical device 100, 200, etc., may be inserted into the patient (either percutaneously or through an "open" surgical procedure) and then coupled to the vasculature of the patient via anastomosis at the lateral ends of lumen 110.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A method of reinforcing a non-natural flow path between a first portion of a vasculature and a second portion of the vasculature, the method comprising:
   obtaining a reinforcing sleeve that is configured to slide over a lumen;
   sliding the reinforcing sleeve along the lumen to a predetermined location; and
   securing the reinforcing sleeve to the lumen by removing an enlarging ring from between the lumen and an end cap of the reinforcing sleeve, such that the end cap comprises an inner diameter less than an outer diameter of the lumen.

2. The method of claim 1, further comprising coupling a first end of the lumen to the first portion of the vasculature.

3. The method of claim 2, further comprising coupling a second end of the lumen to the second portion of the vasculature.

4. The method of claim 1, further comprising:
   providing a second reinforcing sleeve that is configured to slide over the lumen; and
   sliding the second reinforcing sleeve along the lumen to a second predetermined location.

5. The method of claim 1, further comprising applying a push force to the reinforcing sleeve to slide the reinforcing sleeve along the lumen to the predetermined location.

6. The method of claim 1, further comprising adjusting a length of the reinforcing sleeve.

7. A non-natural flow path system between a first portion of a vasculature and a second portion of the vasculature, the system comprising:
   a lumen, wherein a first end of the lumen is configured to couple to the first portion of the vasculature and a second end of the lumen is configured to couple to the second portion of the vasculature; and
   a reinforcing sleeve configured to slide along the lumen to a predetermined position, the reinforcing sleeve comprising:
      an end cap disposed at an end of the reinforcing sleeve; and
      an enlarging ring removably disposed between the lumen and the end cap.

8. The system of claim 7, wherein a crush force of the reinforcing sleeve is greater than a crush force of the lumen.

9. The system of claim 7, wherein the reinforcing sleeve is bendable at least up to 180 degrees.

10. The system of claim 7, wherein the reinforcing sleeve comprises a metal alloy.

11. The system of claim 10, wherein the reinforcing sleeve is braided.

12. The system of claim 10, wherein the reinforcing sleeve is helically wound.

13. The system of claim 10, wherein the reinforcing sleeve opens when accessed with a needle.

14. The system of claim 10, wherein the reinforcing sleeve further comprises a pair of end caps at opposing ends of the reinforcing sleeve.

15. The system of claim 14, wherein the end caps are silicone.

16. The system of claim 7, wherein the lumen comprises a layer that is an extruded elastomeric tube.

17. The system of claim 7, wherein the lumen comprises porous PTFE.

18. The system of claim 7, further comprising a second reinforcing sleeve.

19. A non-natural flow path system between a first portion of a vasculature and a second portion of the vasculature, the system comprising:
   a lumen, wherein a first end of the lumen is configured to couple to the first portion of the vasculature, and a second end of the lumen is configured to couple to the second portion of the vasculature, wherein the lumen comprises a layer that is an extruded elastomeric tube; and
   a reinforcing sleeve configured to slide along the lumen to a predetermined position, the reinforcing sleeve comprising:
      an end cap disposed at an end of the reinforcing sleeve; and
      an enlarging ring removably disposed between the lumen and the end cap.

20. The system of claim 19, wherein the layer self-seals.

* * * * *